US008603542B2

(12) United States Patent
Bartels

(10) Patent No.: US 8,603,542 B2
(45) Date of Patent: *Dec. 10, 2013

(54) VETERINARY TOPICAL AGENT

(75) Inventor: Jennifer Bartels, Hammond, LA (US)

(73) Assignee: Penguin IP Holdings Inc., Hammond, LA (US)

(*) Notice: Subject to any disclaimer, the term of this patent is extended or adjusted under 35 U.S.C. 154(b) by 269 days.

This patent is subject to a terminal disclaimer.

(21) Appl. No.: 12/879,633

(22) Filed: Sep. 10, 2010

(65) Prior Publication Data

US 2011/0189160 A1 Aug. 4, 2011

Related U.S. Application Data

(63) Continuation-in-part of application No. 12/700,375, filed on Feb. 4, 2010.

(51) Int. Cl.
*A01N 59/08* (2006.01)
*A61K 33/14* (2006.01)

(52) U.S. Cl.
USPC .......................................................... 424/677

(58) Field of Classification Search
None
See application file for complete search history.

(56) References Cited

U.S. PATENT DOCUMENTS

| 4,443,437 | A | 4/1984 | Prokosch et al. |
| 4,725,271 | A | 2/1988 | Korol |
| 4,952,402 | A | 8/1990 | Sparks et al. |
| 5,747,058 | A | 5/1998 | Tipton et al. |
| 5,851,556 | A | 12/1998 | Breton et al. |
| 5,993,830 | A | 11/1999 | Freij |
| 6,123,953 | A | 9/2000 | Greff |
| 6,328,983 | B1 | 12/2001 | Afriat |
| 6,541,042 | B1 | 4/2003 | Frater-Schrder et al. |
| 6,544,530 | B1 | 4/2003 | Friedman |
| 6,548,075 | B1 | 4/2003 | Bengs et al. |
| 6,670,407 | B2 | 12/2003 | Howdle et al. |
| 2006/0115438 | A1* | 6/2006 | Vonbehren et al. ............. 424/59 |
| 2008/0260864 | A1* | 10/2008 | Dascalu ........................ 424/685 |

FOREIGN PATENT DOCUMENTS

WO  WO/2005/112910  1/2005

OTHER PUBLICATIONS

Marta, Aquaphor and petroleum safety, Mar. 12, 2008; [online] [downloaded on Sep. 23, 2012 from http://www.truthinaging.com/face/aquaphor-and-petroleum-safety].*
Briggs, Skin Deep, The Horse, Jan. 2009, pp. 35-39, unattributed, A sensitive skin to protect, royalcanin.com, 2006.

* cited by examiner

*Primary Examiner* — Abigail Fisher
*Assistant Examiner* — Thor Nielsen
(74) *Attorney, Agent, or Firm* — Todd L. Juneau

(57) ABSTRACT

Methods and compositions for treating skin conditions in animals, which tend to have higher skin pH than humans, including wounds, ulcers, rashes, burns, abrasions, and other irritations and relevant injuries are provided. The invention contemplates the use of an aqueous or emollient medium having non-occlusive properties with one or more pH raising ingredients in a composition specifically designed to deliver oxygen to the skin's surface.

7 Claims, No Drawings

VETERINARY TOPICAL AGENT

CROSS REFERENCE TO RELATED APPLICATIONS

This application is a continuation-in-part of Ser. No. 12/700,375, filed Feb. 4, 2010, claiming priority under 35 USC 120, the entire contents of which are incorporated herein by reference in its entirety.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

REFERENCE TO A SEQUENCE LISTING

Not applicable.

FIELD OF THE INVENTION

This invention relates to methods and compositions for both oxygenating and delivering an environment of elevated pH adjustment to the the skin of animals in order to treat skin disorders, illnesses, injuries and irritations.

BACKGROUND OF THE INVENTION

The ability to provide oxygen to skin tissue is critical for many skin conditions in animals, including wounds, rashes, ulcers, saddle sores, burns, and abrasions. Insufficient oxygenation of compromised tissue will result in slow healing, infections, scar development, and in the worst cases, tissue death and amputation.

The effect of oxygen tension on wound healing has been extensively studied. (For a review, see Whitney, J. D. (1989)). Wound healing is dependent upon several processes including proliferation of fibroblasts, collagen synthesis, angiogenesis and re-epithelialization. Animal studies have shown that several of these processes are affected by the subcutaneous partial pressure of oxygen ($O_2$). For example, supplemental oxygen can lead to increased rate of collagen deposition, epithelialization and improved healing of split thickness grafts. Increased subcutaneous oxygen has also been shown to improve bacterial defenses.

Various methods of administration of oxygen gas in humans, either through inhalation of the gas, or by topical treatment with the gas have been disclosed, including administering oxygen gas to a patient in a hyperbaric chamber.

While a lack of oxygenation can be one cause of skin inflammation in both animals and humans, a second source of causality can be a lowered pH, or reduction, of the skin. While mammalian animals and humans share the same skin compositions and healing processes, mammalian animals sometimes have higher skin pH levels than do humans. For example, healthy horse skin tends to have pH levels around 7.4, and different breeds of dogs can have skin pH levels ranging from approximately 6.8 to 8.6, while the average human skin pH is approximately 4.8. Acidification of skin is associated with diaper rashes and bedsores in humans, and is also associated with conditions such as skin hot spots on dogs and saddle sores on horses, as well as other skin conditions and wounds.

Experts in the veterinary field have long held that alkaline treatments to both human and animal skin make the skin more susceptible to bacterial and fungal infections, such as rain rot and ringworm, as alkaline agents neutralize the skin's acid mantle, which has been seen as critical protection against such infections (see, Skin Deep, by Dr. Eric Witherspoon, TheHorse.com, January 2009, and A sensitive skin to protect, publications.royalcanine com).

Increased pH is also thought to be a symptom of any number of skin conditions, including eczema, contact dermatitis and atypical dermatitis (see, *Alkaline pH Skin Problems*, Andra Moldav, Apr. 20, 2010). For these reasons, nearly all pH-adjusting skin compositions, both for human and veterinary uses, have tended towards formulation for reduced, not increased, pH.

Dermatitis develops when the skin is subjected to conditions that breakdown the stratum corneum. The stratum corneum is the outer layer of skin and is composed of multiple layers of keratinocytes, with the number of layers varying according to the age and species of animal. The main purpose of this part of the skin is to reduce water loss, repel microbial infection, protect deeper layers, and provide a water-repellant layer. Damage to this layer can occur, for example, when an animal's skin is exposed to agents that lower the skin pH and result in the breakdown of the stratum corneum. Although moisture alone will loosen this layer and allow for friction irritation to occur, breakdown by agents such as urine and fecal enzymes can reduce, or acidify, the skin resulting in chemical irritation. Further, animals are more likely than humans to cause secondary irritation and abrasions by scratching and biting at already-irritated skin.

Environmental hazards such as moisture, contact with bacteria infused water, injuries from skin scratching, shampoo and/or other detergents and skin treatments can cause irritation and hot spots. More specifically, friction or pressure weakens the stratum corneum and eventually causes injury in both humans and animals. These wounds have been found to be at a lower pH than the recognized healthy norm for the relevant animal. Therefore, upward adjustment to the pH of the wound or skin irritation often provides an opportunity for healing. In this regard, the pH levels of skin are comparable to the effects of lowered pH in aquatic environments, which results in lower levels of oxygen content in water, thereby damaging or destroying both aquatic plant and animal life.

Despite the weight of expert opinion in the field against the use of pH-increasing skin products, it is known that increased pH levels and oxygenation promote healing of wounds or skin conditions, whether such conditions arise from external stimuli or from internal processes, such as allergic dermatitis or eczema. In either case, the symptoms may respond positively to a pH raised environment both in counteracting acidification of the skin and in providing increased oxygenation via the higher pH composition.

Pressure-inflicted skin conditions such as saddle sores on horses or collar sores on cats and dogs, like bedsores in human hospital patients, can occur when the skin is exposed to friction, moisture and a lack of oxygenation over an extended period of time. Under such conditions, irritation legions appear at the pressure points on the skin, such as the withers and girth of a horse or neck skin underlying a dog or cat's collar. The wound healing process, depending on the type of injury to the skin, is an intricate process that involves the steps of inflammation, proliferation, and remodeling. During inflammation, bacteria and debris are phagocytized and removed, and factors are released that cause the migration and division of cells involved in the proliferative phase.

The proliferative phase is characterized by angiogenesis, deposition of collagen, formation of granular tissue, re-epithelialization, and wound contraction. In angiogenesis, new blood vessels are formed by vascular endothelial cells. In fibroplasia and formation of granular tissue, fibroblasts grow and form a new, provisional extracellular matrix (ECM) by secreting collagen and fibronectin.

Simultaneously, re-epithelialization occurs, providing a new epithelial layer. It is at this stage that oxygenation of the skin is critical to wound healing.

In the remodeling phase, collagen is remodeled and realigned along tension lines and cells that are no longer needed are removed by apoptosis.

Common treatments for the types of skin conditions described hereinabove include use of zinc oxide pastes, powders, petroleum-based creams, and even mild steroid creams to reduce excess moisture, provide antibacterial activity or barriers, and to reduce damage caused by the body's own inflammatory processes. Conventionally, such treatments include a barrier, or "occlusive" component. The purpose of these is to provide a film on the skin and thereby create a layer, which is impermeable to external irritants. Thus, this kind of skin preparation relies on the principle of occlusion, which means that a covering layer is provided on the skin, thereby constituting a certain degree of protection as long as it remains in place. Typically, such occlusive barrier agents are also impermeable to both water and oxygen.

One disadvantage of an occlusive treatment is that even a very small mechanical influence, such as contact that may arise between the skin and clothes, will remove the layer of ointment and thereby eliminate the protecting barrier. Other disadvantages of occlusive barrier ointments are that, due to the impermeability thereof, they increase the body temperature of the user and trap both perspiration and sebum against the skin, thereby further acidifying the skin. Consequently, there is a need of different preparations adapted for different substances, which the user may contact and which are permeable or oxygen and, perhaps, water, while remaining non-permeable to potential irritants.

While some treatments have focused on an antibacterial approach or an approach of keeping skin dry, other have focused on pH. For example, U.S. Pat. No. 6,805,875, to Bartels, discloses topical compositions and treatments of a skin condition in humans commonly known as "diaper rash" and more particularly, acidic-type diaper rash and other skin irritations caused by acidic bodily secretions, usually resulting from teething, antibiotic dosages, bacterial infections, and an acidic diet.

U.S. Pat. No. 6,800,292 to Murad, discloses dermatological agents for treating dermatological disorders, including veterinary use. The dermatological agents include a therapeutically effective amount of at least one fruit extract in an amount sufficient to neutralize free radicals, a moisturizing agent in an amount sufficient to facilitate hydration of the skin, and a pharmaceutically acceptable carrier. Such application teaches the use of inorganic bases, include metallic salts made from aluminum, calcium, lithium, magnesium, potassium, sodium, and zinc.

U.S. Pat. No. 6,133,318 to Hart, discloses a single medicine oxalic acid or oxalate composition or "magic bullet" and method of treatment or prevention of warm-blooded animals including humans and pets for infectious or pathogenic microbial, bacterial, or viral disease, preventing of bacterial or viral infections, and the like, is provided which includes at least one therapeutically effective form of oxalic acid or oxalate selected from oxalic acid in a free acid, ester, lactone or salt form and oxalate including sodium oxalate, oxalic acid dihydrate, anhydrous oxalic acid, oxamide, and oxalate salts, natural or processed foods including molds, plants or vegetables containing oxalic acid or oxalate, beverages, liquids or juices containing oxalic acid or oxalate, additives containing oxalic acid or oxalate, and combinations thereof.

U.S. Pat. No. 5,993,830 to Friej, discloses a veterinary skin preparation comprising lipophilic and hydrophilic components, which is intended for application on skin. The skin preparation is characterized in that it exists as a two-phase system and it is capable of creating a semi-permeable membrane in the skin.

U.S. Pat. No. 6,328,983 to Afriat, discloses the use of a silicone gum to stabilize ascorbic acid or one of its esters or salts in a topical composition and to novel compositions comprising these components and having an adjustable pH for use in the field of veterinary medicine.

Accordingly, there is still a need for methods and compositions for veterinary treatment of skin injuries that increase the oxygen delivery to the skin and neutralize acidity of the skin in a convenient and efficient manner.

BRIEF SUMMARY OF THE INVENTION

Methods and compositions for treating skin conditions in animals, which tend to have higher skin pH than humans, including wounds, ulcers, rashes, burns, abrasions, and other irritations and relevant injuries to animals are provided. Animals with elevated skin pH are especially susceptible to skin irritations, rashes, saddle sores and hot spots. The invention contemplates the use of an aqueous or emollient medium having one or more pH raising ingredients in a composition specifically designed to deliver oxygen to the skin's surface.

In one preferred embodiment, a veterinary dermatological composition, comprising: water comprising 20-95% of the total weight of the composition; one or more emollients comprising up to 45% of the total weight of the composition; one or more emulsifiers comprising up to 10% of the total weight of the composition; one or more thickening agents, comprising up to 30% of the total weight of the composition; one or more cosmetic preservatives, comprising up to 7% of the total weight of the composition; optionally, one or more anti-itch agents comprising up to 20% of the total weight of the composition; and one or more pH-adjusting components, comprising up to 55% of the total weight of the composition and selected from the group consisting of magnesium hydroxide, aluminum hydroxide, sodium bicarbonate, calcium carbonate, sodium hydroxide, cesium chloride, lactic acid, citric acid and triethanolamine, wherein the concentration of pH adjusting components adjusts the pH of the composition to within a range of about pH 8.0 to about pH 11.6; and further wherein the weight percentages of all components in the composition totals 100%.

In another preferred embodiment, a veterinary dermatological composition, comprising: water comprising 20-95% of the total weight of the composition; Dimethicone 1.0%-3.0% of the total weight of the composition; one or more emollients from the group comprised of Sorbitol, Sorbitan Sesquioleate and/or Lanolin Alcohol, comprising up to 45% of the total weight of the composition; one or more emulsifiers from the group of either polysorbates or fatty acids and comprising up to 10% of the total weight of the composition; one or more paraffin thickening agents comprising up to 30% of the total weight of the composition; one or more cosmetic preservatives from the group of butylated hydroxytoluene (BHT), ethylhexylglycerine or phenoxyethanol, comprising up to 5% of the total weight of the composition; optionally, one or more anti-itch agents from the group consisting of but not limited to colloidal oatmeal, corticosteroids or pramoxine, comprising up to 5% of the total weight of the composition; and one or more pH-controlling agents, comprising up to 20% of the total weight of the composition and selected from the group consisting of magnesium hydroxide, aluminum hydroxide, sodium bicarbonate, calcium carbonate, sodium hydroxide, cesium chloride, lactic acid, citric acid and triethanolamine, wherein the concentration of pH-adjusting components adjusts the pH of the composition to within a range of about pH 8.0 to about pH 11.6; and further wherein the weight percentages of all components in the composition totals 100%.

In another preferred embodiment, a veterinary dermatological composition comprising: water comprising 20-95% of the total weight of the composition; Dimethicone 1.0%-3.0% of the total weight of the composition; one or more emollients from the group comprising Sorbitol, Sorbitan Sesquioleate and/or Lanolin Alcohol, comprising 3.0%-10% of the total weight of the composition; one or more emulsifiers from the group of polysorbate 20, polysorbate 80, carbomer 940, sorbitan sesquioleate and propylene glycol and comprising up to 1-15% of the total weight of the composition; one or more paraffin thickening agents from the group comprising mineral oil, petrolatum and ceresine wax, comprising 3.0%-10% of the total weight of the composition; optionally, one or more anti-itch agents from the group consisting of colloidal oatmeal, hydrocortisone acetate or pramoxine comprising 0.1-5% of the total weight of the composition; one or more cosmetic preservatives from the group of butylated hydroxytoluene (BHT), ethylhexylglycerine or phenoxyethanol, comprising up to 5% of the total weight of the composition; and one or more pH-controlling agents, comprising 0.1-20% of the total weight of the composition and selected from the group consisting of magnesium hydroxide, aluminum hydroxide, sodium bicarbonate, calcium carbonate, sodium hydroxide, cesium chloride, lactic acid, citric acid and triethanolamine, wherein the concentration of pH adjusting components adjusts the pH of the composition to within a range of about pH 9.0 to about pH 11.6; and further wherein the weight percentages of all components in the composition totals 100%.

In another preferred embodiment, a veterinary dermatological composition comprising: water comprising 30-75% of the total weight of the composition; Dimethicone comprising 1%-3% of the total weight of the composition; Mineral Oil comprising 10%-30% of the total weight of the composition; Petrolatum comprising 3.0%-10% of the total weight of the composition; Ceresine Wax 3.0%-10% of the total weight of the composition; Sorbitol comprising 3.0%-10% of the total weight of the composition; Sorbitan Sesquioleate 3.0%-10% of the total weight of the composition; optionally, Lanolin Alcohol 1.0%-3.0% of the total weight of the composition; optionally, Zinc Oxide 1.0%-3.0% of the total weight of the composition; BHT 0.1%-1.0% of the total weight of the composition; Phenoxyethanol 0.1%-1.0% of the total weight of the composition; Ethylhexylglycerin 0.1%-1.0% of the total weight of the composition; Aluminum Hydroxide 0.1%-10.0% of the total weight of the composition; and Magnesium Hydroxide 0.1%-10.0% of the total weight of the composition; wherein the concentration of Magnesium Hydroxide, Aluminum Hydroxide, or both, adjusts the pH of the composition within a range of about pH 9.0 to about pH 11.6, and wherein the weight percentages of all components in the composition totals 100%.

In another preferred embodiment, the veterinary dermatological composition according to the present invention, wherein the composition has a pH within a range of about pH 9.0 to about pH 11.6.

In another preferred embodiment, the veterinary dermatological composition according to the present invention, wherein the composition has a pH within a range of about pH 9.0 to about pH 10.5.

In another preferred embodiment, the veterinary dermatological composition according to the present invention, in the form of a lotion, cream, emulsion, suspension, ointment, gel, paste, film, bath, soak, spray, stick, powder, or foam.

In another preferred embodiment, the veterinary dermatological composition according to the present invention, in the form of a cream or an ointment.

In another preferred embodiment, the veterinary dermatological composition according to the present invention, in a delivery vehicle selected from a single use, individualized, sterile packet, an aerosol spray, a pump spray, a pre-soaked or infused bandage or dressing, a pre-soaked wipe, an infused film for application to the skin, or an infused sponge with applicator stick for use in oral care to treat mouth sores.

In another preferred embodiment, the veterinary dermatological composition according to the present invention, in combination with an additional therapeutic agent.

In another preferred embodiment, the veterinary dermatological composition herein, wherein the additional therapeutic agent is a disinfectant, including chlorhexadrine, and anti-fungal, including miconazole nitrate, a cooling agent, including aloe, or a coagulant, including thrombin.

In another preferred embodiment, a method for topically increasing the oxygenation of damaged epidermis, comprising the step of topically applying to an animal a dermatologically acceptable composition.

In another preferred embodiment, a method for treating a skin condition, comprising the step of topically applying to an animal a dermatologically acceptable composition. In another preferred embodiment, a method for treating an external wound, comprising the step of topically applying to an animal a dermatologically acceptable composition.

In another preferred embodiment, a method for topically increasing the pH of damaged epidermis, comprising the steps of topically applying to an animal a dermatologically acceptable composition.

In another preferred embodiment, a method of topically applying a dermatologically acceptable composition to an animal for treatment for eczema or dermatitis-like skin rash, such applications to be made every 8-12 hours until such skin condition disappears.

DETAILED DESCRIPTION OF THE INVENTION

Methods and compositions for treating skin conditions in animals, which tend to have higher skin pH than humans, including wounds, ulcers, rashes, burns, abrasions, and other irritations and relevant injuries to animals are provided. The invention contemplates the use of an aqueous or emollient medium having one or more pH raising ingredients in a composition specifically designed to deliver oxygen to the skin's surface.

Approximate skin pH levels for various types of nonhuman animals are as follows: horses 7.0-7.4, cats 6.4, pigs 6.3, goats 8.1, and dogs 6.8-8.6, depending on the breed.

In a preferred embodiment, the pH of the composition ranges from about 8.0 to about 11.0, and more preferably from about 9.0 to about 10.5. In a most preferred embodiment for dogs, the pH ranges from about pH 9.5 to about pH 11.6, depending upon the breed. In a most preferred embodiment for horses, the pH ranges from about pH 10.1 to pH 10.4. In a most preferred embodiment for cats, the pH ranges from about 9.1 to 9.4.

In a preferred embodiment as an ointment, the medium is comprised of one or more pH raising components selected from sodium bicarbonate, calcium carbonate, magnesium hydroxide, aluminum hydroxide, sodium hydroxide, and/or cesium chloride. Additional pH adjusters contemplated herein include lactic acid, citric acid, acetic acid, and triethanolamine. In preferred embodiments where it is MgOH, the wt. is at [0.1%-7.0%, 0.1%-2.0%, or 1.0%]. In preferred embodiments where it is AlOH, the wt. is at [0.1%-7.0%, 0.1%-2.0%, or 1.0%]. In preferred embodiments where it is $Na(CO_2)_3$, the wt. is at [0.1%-30.0%, or 0.1%-20.0%].

In a preferred embodiment, the emollient base contains a range of at least 50% water and/or non-occlusive humectants. In a preferred embodiment, the composition is [70%-80%] water. In another preferred embodiment, the composition is [70%-72%] water. These may act as permeability enhancers and/or carriers for the pH raising component.

Emollients contemplated herein include natural and manmade materials, including mineral oil, petrolatum, sorbitol, sorbitan sesquioleate, dimethicone, cyclomethicone, isopropyl myristate, lactic acid, sodium lactate, sodium hyaluronate, and glycerin.

Emulsifiers contemplated herein include sorbitan sesquioleate, polysorbate including polysorbate 20 and polysorbate 80, propylene glycol, carbomer including carbomer 940, sodium lauryl sulfate, sodium laureth sulfate, cocamidopropyl betaine, cocamide DEA, amonium lauryl sulfate, lauramide DEA, lecithin, emulsifying wax NF, ceresin, microcrystalline wax, waxes used in cosmetics, glyceryl monostearate, starch, palm stearic acid, trienthanolamine, and xanthan gum.

Additional binders, stabilizers, preservatives, colorants, and fragrances, known to a person of ordinary skill in the art, are contemplated as within the scope of this invention. Some preferred additional ingredients include, as examples without being limited thereto, lanolin alcohol including, phenoxyethanol including, ethylhexylglycerin and BHT.

Although not to be limited by a particular theory, it is believed that the alkaline environment and alkaline chemistry act as the source of the oxygen that is provided to the tissues to effectuate the treatment of the wound. Where MgOH is provided, it acts to raise the pH. Where AlOH is also added to MgOH, the AlOH appears to provide for a slow release delivery. It is believed that, in addition to its other properties, the known surfactant dimethicone is reducing the surface tension of the generated oxygen and allowing for longer contact of the raised pH composition with the skin. It is further believed that he non-occlusive properties of dimethicone, in contradistinction to occlusive agents such as paraffins and other known emulsifiers and surfactants, provides increased oxygenation to the affected skin over time, resulting in accelerated and improved healing. The presence of dimethicone allows for a concomitant reduction in the required composition percentage of occlusive agents such as mineral oil and ceresine wax.

The ointments, creams, and salves contemplated herein may be an oil-in-water (OW) emulsion or a water-in-oil (WO) emulsion. The oil phase ingredients are mixed. Heat may be required of wax-blends. The water phase ingredients are also mixed. Processing for an oil-in-water emulsion starts with blending at high speed the water phase and the oil phase is added slowly to allow the emulsion to form. Processing for a water-in-oil emulsion is accomplished by adding the water phase to the oil phase during high speed blending to allow the emulsion to form.

To facilitate understanding of the invention set forth in the disclosure that follows, a number of terms are defined herein.

The term "wound" used herein refers broadly to injuries to the skin and subcutaneous tissue initiated in any one of a variety of ways (e.g., pressure sores from extended contact with saddles or collars, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that exhibits impaired healing parameters interfering with the physiological sequence of events. These wounds tend to prolong and/or halt healing time course, subjecting the wounds to further complications such as recurrent infections and necrosis.

The present invention contemplates treating all skin wound types and of all grades, including deep wounds and chronic wounds, as well as skin damage.

The term "skin wound" refers to any type of epithelial wound including, but not limited to, an ulcer such as a pressure ulcer, a wound resulting from scratching at skin irritations from parasites, yeast infections or other causes, a bite wound, a burn, a sun burn, an aging skin wound, an inflammatory disease wound, a skin blistering wound, a hyperkeratotic wound, a laceration, a surgical incision wound, and a post surgical adhesions wound.

The term "skin damage" as used herein refers to any type of skin damage or condition such as, for example, inflammation, irritation, abrasions, cuts, burns, rashes, scrapes, wounds, auto-immune related damage, infection related damage, and other types of breakdown of the stratum corneum, epidermis, and underlying tissues.

The term "epidermis" refers to the outer most layer of the skin.

Dermatological compositions of the invention may be utilized for treatment of a wide variety of dermal conditions and adverse physiological states manifesting dermally, including, without limitation, skin ulcers, dry skin/xerosis, hyperkeratotic disorders, ichthoyosis, keratosis, keratoderma, dermatitis, seborrheic dermatitis, contact dermatitis, chemical injury, burns from heat, chemicals, electricity, sunlight or radiation, itching, pruritis, eczema, callouses, hot spots, saddle sores, inflammation from skin parasites such as fungi, mites, fleas and ticks, and burn wounds.

The term "healing" in respect to a wound or skin damage refers to a process to repair a wound, or to repair the skin damage.

The phrase "inducing or accelerating a healing process of a skin wound or skin damage" refers to either the induction of the formation of granulation tissue of wound contraction and/or the induction of repithelialization (i.e., the generation of new cells in the epithelium). Wound healing is conveniently measured by decreasing wound area.

As used herein, the phrase "pharmaceutical composition" refers to a preparation of one or more of the active ingredients described herein with other chemical components such as physiologically suitable carriers and excipients. The purpose of a pharmaceutical composition is to facilitate administration of a composition to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of an administered active ingredient. An adjuvant is included under these phrases. A preferred carrier is purified water.

The term "excipient" as used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The various compositions of the invention may be in the form of lotions, creams, emulsions, suspensions, ointments, gels, baths, soaks, sprays, infused dressing, powder, foam, or other suitable forms capable of administration to the skin of an animal. Accordingly, compositions in which water and/or water-miscible solvents are employed in varying amounts, are contemplated. Additionally, the compositions may be formulated with adjuvants, additional active ingredients and/or excipients, and/or other ingredients, to impart specific thixotropy, viscosity, flow, spreading, self-leveling, or other characteristics thereto, as necessary or desirable in specific formulations.

The term "cream" refers to a topical medication form that is an emulsion of oil and water in approximately equal proportions.

The term "ointment" refers a topical medication form that is an oil and water mixture of about 80% oil and about 20% water, without being limited to specific percentages.

The term "lotion" refers to a topical medication form that is low to medium viscosity emulsion, including an oil-in-water emulsion or a water-in-oil emulsion.

The term "gel" refers to a topical medication form that liquifies upon contact with skin.

The term "paste" refers to a topical medication form that is a combination of oil, water, and a powder, i.e an ointment in which the powder is suspended.

Compositions of the invention are usefully employed as skin moisturizers, skin softening agents, skin debridement agents, etc., as well as base compositions for therapeutic, e.g., pharmacological, formulations.

In therapeutic formulations, the compositions of the invention may be utilized as base compositions for topical administration of therapeutic agents such as wound management agents (e.g. sodium chloride, magnesium sulfate, anti-inflammatory agents, e.g., non-steroidal anti-inflammatory agents, glucocorticosteroids (e.g., hydrocortisone, triamcinolone, betametamethasone, or their respective derivatives, or ibupropfen, ketoprofen, methyl salicylate, etc.), anti-infective (antibiotic) agents (e.g., chlortetracycline, oxytetracycline, fusidic acid, silver sulfadiazine, and mixtures thereof), enzymes, anti-fungal agents (e.g. silver sulfadiazine, enilconazole, clotrimazole, ketoconazole, miconazole, povidone-iodine, natamycin and mixtures thereof), anti-viral agents, dermatitis-combating agents, topical immunomodulator agents, etc., as well as any other agents that are beneficially applied to the skin to treat or ameliorate symptoms of physiological disorders and disease states susceptible to such treatment or amelioration, such as for example, zinc oxide.

Set out below is a tabulation of secondary therapeutic agents by category and specific examples, without limitation, for which veterinary dermatological compositions of the invention may be utilized in therapeutic formulations. In the use of such therapeutic agents, the composition of the invention as variously described herein, comprising humectant, emollients and optional additional excipients, is utilized as a base to which the therapeutic agent is added in a therapeutically effective amount to yield a corresponding therapeutic composition for combating the appertaining disease state or adverse physiological condition constituting the specific indication.

Wound Healing

Papain, trypsin, allantoin, chymo-trypsin, streptokinase, streptodornase, ficin, pepsin, carboxypeptidase, amino-peptidase, chymopapain, bromelin.

Anti-Inflammatory

Hydrocortisone, triamcinolone, betametamethasone, ibupropfen, ketoprofen, methyl salicylate, dexamethasone, prednisolone, cortisone, prednisone, beclomethasone, betamethasone, flunisolide, fluocinolone acetonide, fluocinonide, indomethacin, diclofenac sodium, mefenamic acid, azulene, phenacetin, isopropylantipyrine, acetaminophen, bendzac, phenylbutazone, flufenamic acid, sodium salicylate, salicylamide, sasapyrine, etodolac.

Anti-Infectives

Bacitracin, polymixin B, mupirocin, neomycin, tetracyclines (chlortetracycline hydrochloride, oxytetracycline hydrochloride and tetracycline hydrochoride), clindamycin, gentamicin sulfate, benzalkonium chloride, benzethonium chloride, hexylresorcinol, methylbenzethonium chloride, phenol.

Antiseptics

Thymol, Menthol, Benzalkonium Chloride, Chlorhexidine gluconate, and natural oils including Tea Tree Oil.

Anti-Fungals

Miconazole, econazole, tolnaftate, ketoconazole, undecylenic acid, amphotericin, carbol-fuchsin, ciclopirox, clotrimzole, haloprogin, mafenide, naftifine, nystatin, oxiconazole, silver, sulfadiazine, sulconazole, terbinafine, tioconazole, undecylenic acid, salicylic acid, benzoyl peroxide, resorcinol, sulfur, sodium sulfacetamide, retinoic acid, isotretinoin, erythromycin, zinc, retinol, citric acid, and alpha hydroxy acid.

Anti-Virals

Acyclovir, docosanol, pencyclovir, cidofovir, desciclovir, famciclovir, ganciclovir, lobucavir, PMEA, valacyclovir, 2242, PAA, PFA, H2G, sorivudine, trifluridin, tromantadine, adenine, arabinoside, arabinosyladenine-monophosphate, lobucavir.

Topical Immunomodulators

Pimecrolimus, tacrolimus, muramyl dipeptide, cyclosporine, interferons (including alpha, beta, and gamma interferons), interleukin-2, cytokines, tumor necrosis factor, pentostatin, thymopentin, transforming factor beta2, erythropoetin.

As used herein, references to compositional ingredients in percents by weight refers to weight percentages based on the total weight of the composition or formulation.

The compositions of the present invention may be packaged in both large and smaller volume containers. In one embodiment, the composition is provided in single use, individualized, sterile packets. In another embodiment, the composition is provided in a pump spray or aerosol spray container. In another embodiment, the composition is provided in a pre-soaked bandage or dressing, a pre-soaked wipe, or an infused film for application to the skin. In another embodiment, the composition is provided in an infused sponge with applicator stick, especially for use in oral care to treat mouth sores.

EXAMPLES OF COMPOSITIONS

Example 1

Water 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Magnesium Hydroxide <1%, Phenoxyethanol <1%, Ethylhexylglycerin <1%, with a pH between 8.0 and 11.6.

Example 2

Water 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Aluminum Hydroxide <1% wt., Magnesium Hydroxide <1%, BHT <1% wt., Phenoxyethanol <1%, Ethylhexylglycerin <1%, with a pH 8.0-11.6.

Example 3

Water 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Magnesium Hydroxide 0.1-7.0%, Phenoxyethanol <1%, Ethylhexylglycerin <1%, with a pH 9.5-11.6.

Example 4

Water 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Aluminum Hydroxide 0.1-7.0% wt., Magnesium Hydroxide 0.1-7.0, BHT <1% wt., Phenoxyethanol <1%, Ethylhexylglycerin <1%, with a pH 10.1-10.4.

Example 5

Water 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Sodium Bicarbonate 1-30% w/ Citric acid to buffer to 9.2, Phenoxyethanol <1%, Ethylhexylglycerin <1%, with a pH 9.0-11.6.

Example 5

Water 20-95% wt., Mineral Oil 10-30% wt., Petrolatum 3-10% wt., Sorbitol 3-10% wt., Ceresine Wax 3-10% wt., Sorbitan Sesquioleate 3-10% wt., Dimethicone 1-3% wt., Sodium Bicarbonate 1-30% w/Citric acid to buffer to 9.2, Phenoxyethanol <1%, Ethylhexylglycerin <1%, with a pH 9.1-9.4.

Example 6

Water 20-95% wt., Mineral Oil 10-30% wt., Petrolatum 3-10% wt., Sorbitol 3-10% wt., Ceresine Wax 3-10% wt., Sorbitan Sesquioleate 3-10% wt., Dimethicone 1-3% wt., Calcium Carbonate 1-30%, Phenoxyethanol <1%, Ethylhexylglycerin <1%, with a pH 9.5-10.5.

Use of the Invention: Examples of Treatment

Example 7

Eczema-Like Rash

Cream was applied to lab mix dog with skin rash which appeared to be a condition similar to human eczema. With 1-2 applications, skin rash was alleviated and within 2 days, the skin rash, which had been attempted to be solved using all other available products, went away.

Example 8

Dog Dermatitis

Cream was applied to pug displaying allergic dermatitis symptoms: biting, scratching, yelping with pain. Tail area had been bright red, almost bloody, and dog was subjected to 2 rounds of prescription steroids, which did not alleviate the rash. After 2-3 applications of cream, dog's hair showed regrowth (one application at night) and symptoms were alleviated for 8-10 hours continually after application. Skin appears normal but reapplication continues. Symptoms continue to persist, suggesting continuing allergic reaction, but twice daily reapplication of cream continues to alleviate symptoms.

Example 9

Pressure Wound/Ulcer

Dog shows signs of a pressure wound from a collar rubbing skin underneath, similar to decubitus ulcer in humans or saddle sore in horses. Cream maintains reduction of redness and alleviates irritation from that rubbing/pressure sore upon each application of cream.

Example 10

Ear Yeast Infections

Dog suffers from yeast ear infections irritations. An acidic mixture was prescribed by the veterinarian, and was used for 3 months with no result. After 1-2 applications of cream, symptoms alleviated, as yeast does not thrive in high pH environment.

Example 11

Dog Hot Spots

Golden Retriever had open hot spots which are red, seeping, and have an odor. After one application of cream overnight, the hot spot appears to be sealed and continues to improve. Appearance of skin regeneration within 24 hours. Symptoms relieved and dog's scratching, which was exacerbating the condition, stops, therefore creating an additional feature of the treatment in that the sore is not being reopened by the scratching.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

I claim:

1. A dermatological composition, comprising the following components:
   a) water comprising 30 to 75% of the total weight of the composition;
   b) Dimethicone comprising 1% to 3% of the total weight of the composition;
   c) Mineral Oil comprising 10% to 30% of the total weight of the composition;
   d) Petrolatum comprising 3.0% to 10% of the total weight of the composition;
   e) Ceresine Wax comprising 3.0% to 10% of the total weight of the composition;
   f) Sorbitol comprising 3.0% to 10% of the total weight of the composition;
   g) Sorbitan Sesquioleate comprising 3.0% to 10% of the total weight of the composition;
   h) optionally, Lanolin Alcohol comprising 1.0% to 3.0% of the total weight of the composition;
   i) optionally, Zinc Oxide comprising 1.0% to 3.0% of the total weight of the composition;
   j) BHT comprising 0.1% to 1.0% of the total weight of the composition;
   k) Phenoxyethanol comprising 0.1% to 1.0% of the total weight of the composition;
   l) Ethylhexylglycerin comprising 0.1% to 1.0% of the total weight of the composition;
   m) Aluminum Hydroxide comprising 0.1% to 10.0% of the total weight of the composition; and
   n) Magnesium Hydroxide comprising 0.1% to 10.0% of the total weight of the composition;
   wherein the concentration of Magnesium Hydroxide, Aluminum Hydroxide, or both, adjusts the pH of the composition within a range of about pH 9.0 to about pH 11.6 to raise the effectiveness of the treatment on animals; and wherein the weight percentages of all components in elements a) through n) in the composition totals 100%.

2. The composition according to claim 1, in combination with an additional therapeutic agent.

3. The composition according to claim 2, wherein the additional therapeutic agent is chlorhexadine, miconazole nitrate, aloe, or thrombin.

4. A method for treating a veterinary skin condition, comprising the step of topically applying to an animal a dermatologically acceptable composition according to claim 2 wherein the veterinary skin condition is eczema, dermatitis, pressure wound, ear yeast infection, or dog hot spots.

5. A method for topically increasing the pH of damaged epidermis, comprising the steps of topically applying to an animal a dermatologically acceptable composition according to claim 1.

6. A method of topically applying a dermatologically acceptable composition according to claim 1 to an animal for treatment of a skin wound or abrasion, comprising applying the composition every 8-12 hours until such skin condition disappears.

7. A method of topically applying a dermatologically acceptable composition according to claim 1 to an animal for treatment of hot spots, saddle sores or other pressure wounds or ulcers, comprising applying the composition made every 8-12 hours until such condition disappears.

* * * * *